US012569701B2

(12) United States Patent
Talakoub et al.

(10) Patent No.: US 12,569,701 B2
(45) Date of Patent: *Mar. 10, 2026

(54) QUALITY ASSURANCE FOR DOSING IN RADIOTHERAPY

(71) Applicant: SIEMENS HEALTHINEERS INTERNATIONAL AG, Steinhausen (CH)

(72) Inventors: Amir Talakoub, Marblehead, MA (US); Stefan Thieme-Marti, Windisch (CH)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 134 days.

This patent is subject to a terminal disclaimer.

(21) Appl. No.: 18/239,110

(22) Filed: Aug. 28, 2023

(65) Prior Publication Data

US 2025/0073499 A1 Mar. 6, 2025

(51) Int. Cl.
*A61N 5/10* (2006.01)

(52) U.S. Cl.
CPC ......... *A61N 5/1039* (2013.01); *A61N 5/1064* (2013.01)

(58) Field of Classification Search
CPC ............................ A61N 5/1039; A61N 5/1064
See application file for complete search history.

(56) References Cited

U.S. PATENT DOCUMENTS

| | | | |
|---|---|---|---|
| 2008/0002811 A1 | 1/2008 | Allison | |
| 2016/0279444 A1 | 9/2016 | Schlosser | |
| 2025/0073499 A1 | 3/2025 | Talakoub et al. | |
| 2025/0073500 A1 * | 3/2025 | Talakoub | ............. A61N 5/1038 |

FOREIGN PATENT DOCUMENTS

| | | |
|---|---|---|
| WO | 2007/014093 A2 | 2/2007 |
| WO | 2007/014093 A3 | 2/2007 |
| WO | 2009/055801 A2 | 4/2009 |

(Continued)

OTHER PUBLICATIONS

Non-Published Commonly Owned U.S. Patent Application, "Treatment Adaptation in Radiotherapy Based On Intra-Fraction Dosing", Filed on Aug. 28, 2023, Siemens Healthineers International AG.

(Continued)

*Primary Examiner* — Jurie Yun
(74) *Attorney, Agent, or Firm* — SU IP CONSULTING

(57) ABSTRACT
A computer-implemented method of determining dose delivered by a radiotherapy system to a plurality of locations within a region of patient anatomy includes: during a first time segment of a treatment fraction, causing the radiotherapy system to be in a first machine state; during the first time segment, delivering radiation to the region of patient anatomy; generating a first surface map for the region of patient anatomy based on surface measurements acquired during the first time segment; generating a first modified digital volume of the region based on the first surface map; and for each of the plurality of locations within the region of patient anatomy, determining a first radiation dose that is delivered to the location during the first time segment, wherein the first radiation dose is based on the first machine state of the radiotherapy system and the first modified digital volume.

20 Claims, 15 Drawing Sheets

(56)             References Cited

FOREIGN PATENT DOCUMENTS

| WO | 2009/055801 | A3 | 4/2009 |
| WO | 2014/096993 | A1 | 6/2014 |
| WO | 2022/036442 | A1 | 2/2022 |
| WO | 2022/144199 | A1 | 7/2022 |

OTHER PUBLICATIONS

International Search Report and Written Opinion of the International Searching Authority, International application No. PCT/EP2024/073569, Nov. 8, 2024.
The Extended European Search Report, application No. 24195865.1, Jan. 29, 2025.
Mark Foskey et al., "Large Deformation Three-Dimensional Image Registration in Image-Guided Radiation Therapy", Institute of Physics Publishing—Physics in Medicine and Biology, Dec. 2005, pp. 5869-5892, vol. 50.

* cited by examiner

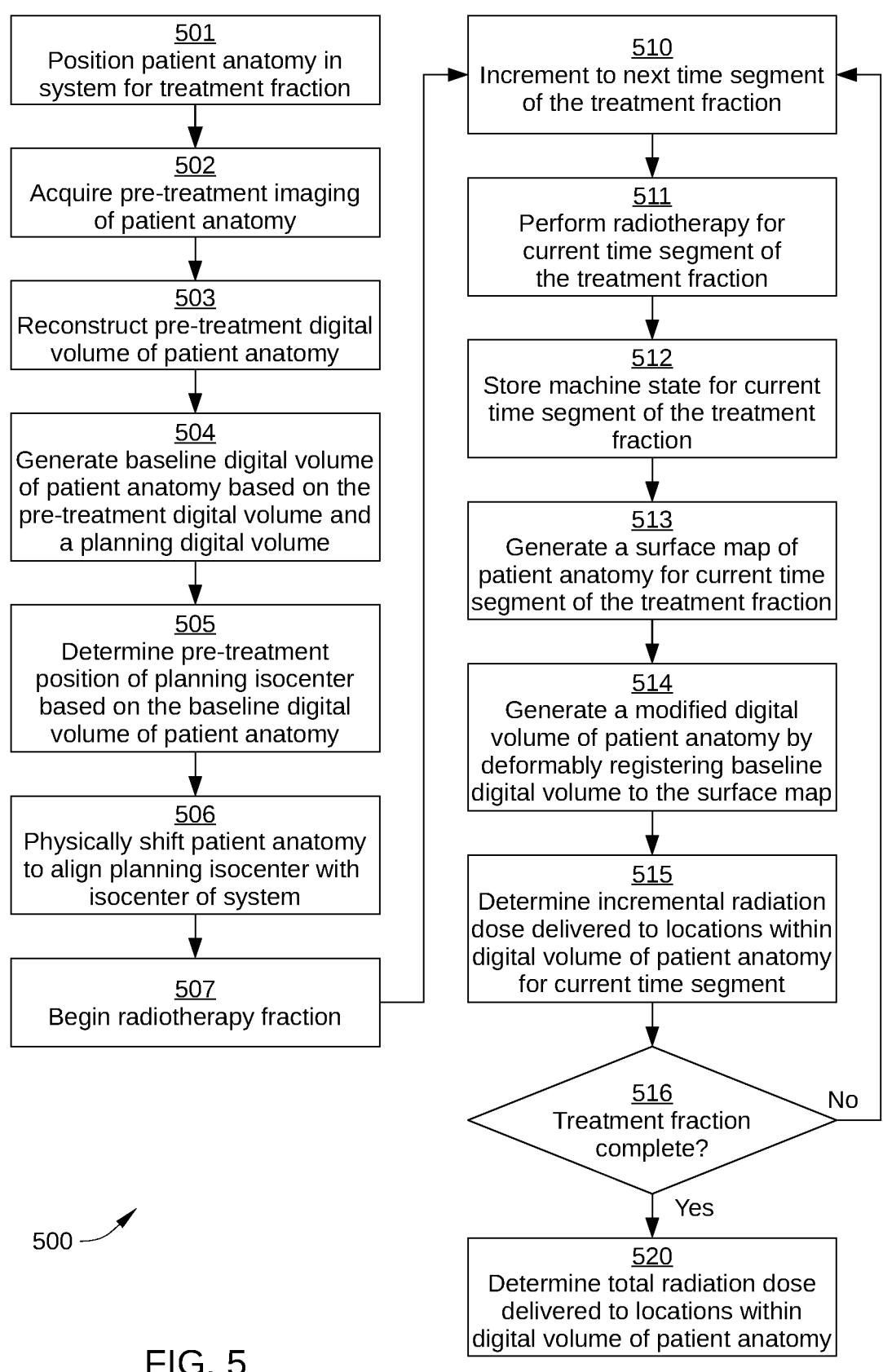

501
Position patient anatomy in system for treatment fraction

502
Acquire pre-treatment imaging of patient anatomy

503
Reconstruct pre-treatment digital volume of patient anatomy

504
Generate baseline digital volume of patient anatomy based on the pre-treatment digital volume and a planning digital volume

505
Determine pre-treatment position of planning isocenter based on the baseline digital volume of patient anatomy

506
Physically shift patient anatomy to align planning isocenter with isocenter of system

507
Begin radiotherapy fraction

510
Increment to next time segment of the treatment fraction

511
Perform radiotherapy for current time segment of the treatment fraction

512
Store machine state for current time segment of the treatment fraction

513
Generate a surface map of patient anatomy for current time segment of the treatment fraction

514
Generate a modified digital volume of patient anatomy by deformably registering baseline digital volume to the surface map

515
Determine incremental radiation dose delivered to locations within digital volume of patient anatomy for current time segment

516
Treatment fraction complete?

No

Yes

520
Determine total radiation dose delivered to locations within digital volume of patient anatomy

QUALITY ASSURANCE FOR DOSING IN RADIOTHERAPY

CROSS-REFERENCE TO RELATED APPLICATION

The present application is related in subject matter to the United States Patent Application titled, "Treatment Adaptation in Radiotherapy Based on Intra-Fraction Dosing" filed on Aug. 28, 2023, and having Ser. No. 18/239,112. The subject matter of this related application is hereby incorporated herein by reference.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to radiation therapy, an imaging system is typically employed to provide a three-dimensional image of the target tissue and surrounding area, referred to as the "treatment planning image." From such imaging, the size and mass of the target tissue can be estimated, a planning target volume determined, and an appropriate treatment plan generated.

So that the prescribed dose is correctly supplied to the planning target volume (i.e., the target tissue) during radiation therapy, immediately before a radiation treatment session (or fraction), the patient is correctly positioned relative to the linear accelerator that provides the radiation therapy. Typically, dosimetric and geometric data are checked before and during the treatment fraction, so the patient is correctly positioned and the administered radiotherapy treatment matches the previously planned treatment. This process is referred to as image guided radiation therapy (IGRT), and involves the use of an imaging system to view target tissues immediately before, and in some cases during, delivery of radiation to the planning target volume. Before delivery of radiation, IGRT uses imaging coordinates from the treatment plan to ensure the patient is properly aligned for treatment in the radiation therapy device. Generally, the target tissues are viewed using a reconstructed region of patient anatomy that is generated based on X-ray images of the region, which are acquired immediately preceding the radiation treatment session.

SUMMARY

According to various embodiments, actual dose delivered by a radiotherapy system to locations within a region of patient anatomy is calculated for each of a plurality of time segments making up a single radiation therapy fraction. The novel dose calculation is based on a time-resolved machine state of the radiotherapy system for each time segment and a time-resolved patient surface that is captured at each time segment of the treatment fraction. A total dose delivered to each location within the region of patient anatomy can then be determined based on the delivered dose that is calculated for each of the time segments.

In some embodiments, a computer-implemented method of determining dose delivered by a radiotherapy system to a plurality of locations within a region of patient anatomy includes: during a first time segment of a treatment fraction, causing the radiotherapy system to be in a first time-resolved machine state; during the first time segment, delivering radiation to the region of patient anatomy; generating a first surface map for the region of patient anatomy based on surface measurements acquired during the first time segment; generating a first modified digital volume of the region based on the first surface map; and for each of the plurality of locations within the region of patient anatomy, determining a first radiation dose that is delivered to the location during the first time segment, wherein the first radiation dose is based on the first time-resolved machine state of the radiotherapy system and the first modified digital volume.

In some embodiments, a computer-implemented method of radiotherapy for a plurality of locations within a region of patient anatomy includes: determining a first total radiation dose that is delivered during a first treatment fraction to a first location included in the plurality of locations, wherein the first total radiation dose is based on a first time-resolved machine state of a radiotherapy system associated with the first treatment fraction, and a time-resolved surface map of the region associated with the first treatment fraction; based on the first total radiation dose, determining a dose error associated with the first location for the first treatment fraction; based on the dose error, determining a second total radiation dose to be delivered to the first location in a second treatment fraction; based on the second total radiation dose, changing a time-resolved machine state of the radiotherapy system associated with the second treatment fraction to a modified time-resolved machine state; and delivering the second total radiation dose to the first location using the modified time-resolved machine state.

Further embodiments include a non-transitory computer-readable storage medium comprising instructions that cause a computer system to carry out one or more of the above methods, as well as a computer system configured to carry out one or more of the above methods.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

FIG. 5 sets forth a flowchart of a computer-implemented method for determining radiation dose delivered by a radiotherapy system to a plurality of locations within a region of patient anatomy, according to one or more embodiments.

DETAILED DESCRIPTION

Figure 1:
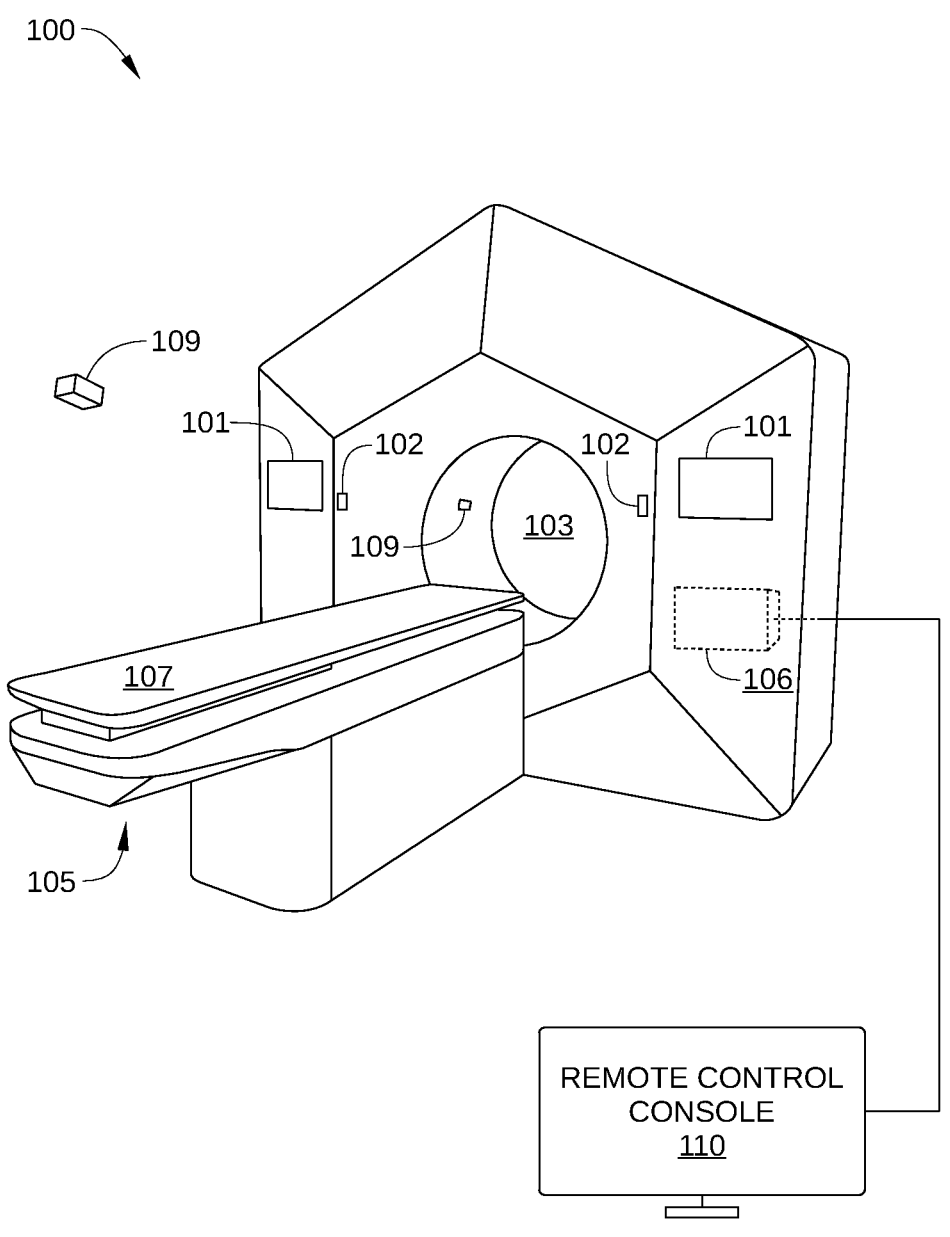
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Introduction

As noted previously, image-guided radiation therapy (IGRT) is frequently employed to facilitate a prescribed dose being correctly supplied to a planning target volume. In IGRT, patient motion and/or changes in the shape or position of the planning target volume can be a significant factor in the efficacy of radiotherapy, and therefore steps are taken to minimize or monitor patient motion. For example, patients are frequently immobilized via pre-formed molds, masks, or other positioning hardware to reduce motion. Further, in some instances, motion caused by patient breathing is controlled or restricted with breath-hold techniques, spirometers, belts, and/or the like. However, even when such motion-reduction measures are employed, patient motion and/or changes in the shape or location of a planning target volume can occur during a treatment fraction. Currently, using conventional techniques to quantify the impact of such motion and/or anatomical changes on the total accumulation of dose in a planning target volume or organs at risk (OARs) is difficult to account. For example, current daily quality assurance (QA) methods for dose delivery typically reconstruct the delivered dose based on system log files for a radiation treatment session that indicate exactly where dose was delivered relative to the isocenter of the system delivering the dose. Such an approach can ensure that the planned dose was delivered relative to the system isocenter as expected. However, if the patient has moved between the time the treatment begins and ends, there is no record of the impact of such movement on the dose to the target or healthy tissue.

In light of the above, there is a need in the art for improved techniques for tracking actual dose delivered in radiotherapy.

According to various embodiments, actual dose delivered by a radiotherapy system to locations within a region of patient anatomy is calculated for each of a plurality of time segments making up a single radiation therapy session (or fraction). The novel dose calculation is based on a time-resolved machine state of the radiotherapy system for each time segment and a time-resolved patient surface that is captured at each time segment of the treatment fraction. A total dose delivered to each location within the region of patient anatomy can then be determined based on the delivered dose that is calculated for each of the time segments. In some embodiments, the novel dose calculation facilitates dosing quality assurance (QA), in which subsequently planned treatment fractions are changed to compensate for out-of-spec dosing during a completed treatment fraction. In some embodiments, the novel dose calculation facilitates adaptive treatment during a particular treatment fraction. In such embodiments, a planned treatment fraction can be changed on-the-fly to compensate for out-of-spec dosing that has occurred earlier in that particular treatment fraction. Various example embodiments are described below.

System Overview

FIG. 1 is a perspective view of a radiation therapy system 100 that can beneficially implement various embodiments. In some embodiments, radiation therapy (RT) system 100 includes an imaging system configured to image patient anatomy using X-ray imaging techniques. For example, in some embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection. In yet other embodiments, any imaging system capable of generating two-dimensional (2D) projection X-ray images, for example as part of a cone-beam computed tomography (CBCT) process, can beneficially implement the various embodiments described herein. In another example of such an embodiment, radiation therapy system 100 can be configured with an imaging system having an MRI-based imaging capability.

Generally, RT system 100 is capable of kV imaging of a target volume immediately prior to or during application of an MV treatment beam, so that an IGRT and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

In some embodiments, RT system 100 further includes one or more patient-monitoring sensors 109. Patient-monitoring sensors 109 can be incorporated into a patient position-monitoring system or surface image guidance system (not shown) that can generate a surface map of the surface of a patient positioned on couch 107. In some embodiments, patient-monitoring sensors 109 can include stereo vision cameras, time-of-flight sensors, surface scanners, and/or the like for computing a live 3D mesh of a surface of a patient positioned on couch 107. Thus, the patient position-monitoring system or surface image guidance system that includes patient-monitoring sensors 109 can be used for the setup of a patient and/or patient positioning accessories, interfraction positioning, and intrafraction patient motion management. For example, in some instances, when the position of a patient on couch 107 exceeds a predefined offset threshold during treatment, a treatment beam can be automatically turned off. In some embodiments, the patient position-monitoring or surface image guidance system that includes patient-monitoring sensors 109 is incorporated in RT system 100. In other embodiments, the patient position-monitoring or surface image guidance system can be a system external to but communicatively coupled to RT system 100.

According to various embodiments, the patient position-monitoring or surface image guidance system that includes patient-monitoring sensors 109 is employed to generate a surface map of the patient a plurality of times during a radiotherapy treatment fraction. Thus, in such embodiments, patient-monitoring sensors 109 is employed to generate a time-resolved surface of patient anatomy that can facilitate determining radiation dose delivered by RT system 100 to a plurality of locations within a region of patient anatomy. Such embodiments are described in greater detail below.

Figure 2:
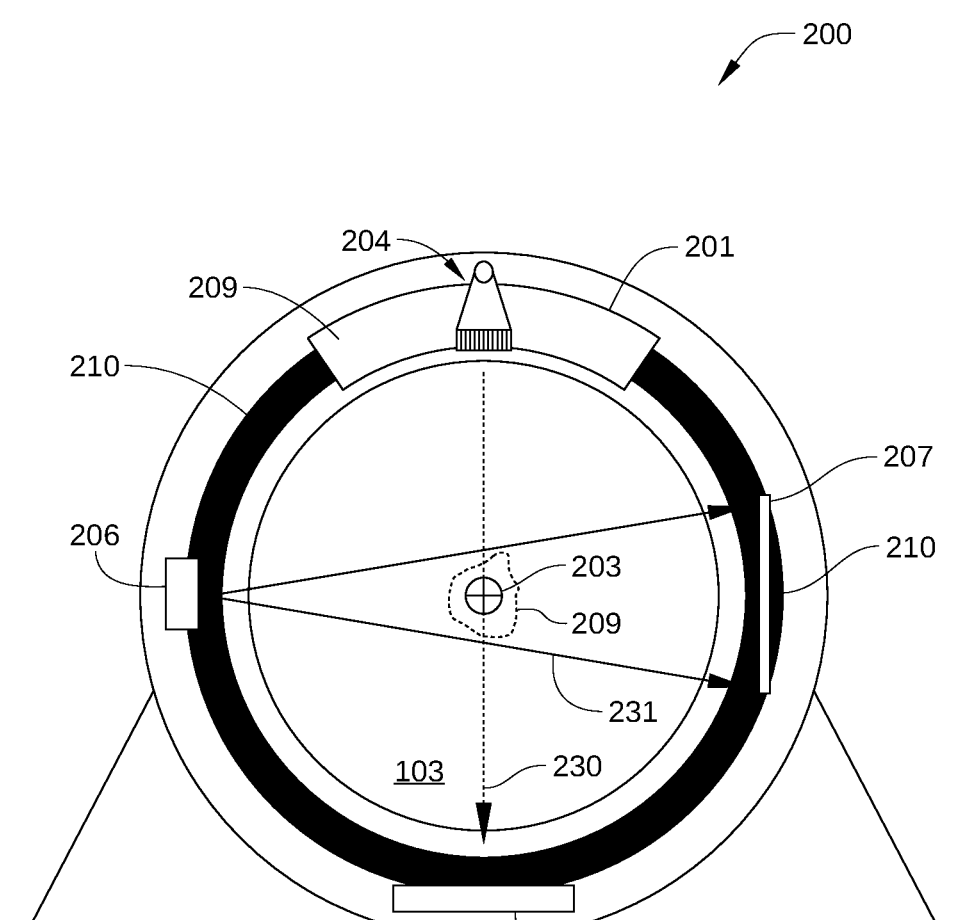
FIG. 2 schematically illustrates a drive stand and gantry of the radiation therapy system of FIG. 1, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, CBCT and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
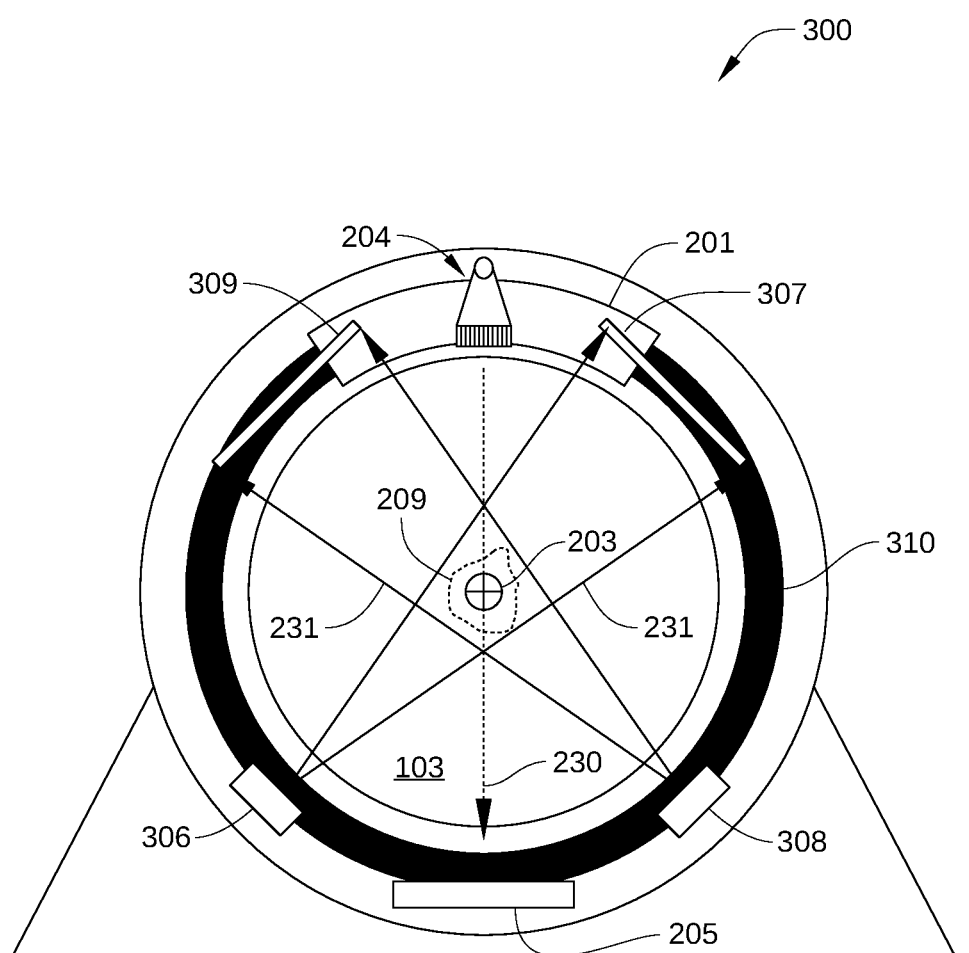
FIG. 3 schematically illustrates a drive stand and a gantry of the radiation therapy system of FIG. 1, according to various embodiments.

FIG. 3 schematically illustrates a drive stand 300 and gantry 310 of RT system 100, according to various embodiments. Drive stand 300 and gantry 310 are substantially similar in configuration to drive stand 200 and gantry 200 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, in some instances, when RT system 100 includes two X-ray imagers and corresponding X-ray sources, sufficient information can be collected to reconstruct a 3D region that includes target volume 309 without rotating gantry 310. Alternatively, in some instances, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 in FIG. 2 (or by first x-ray imager 307 and second X-ray imager 309 in FIG. 3) are used to reconstruct a 3D digital volume of an object or portion of patient anatomy, such as a 3D region of patient anatomy that includes target volume 209. One embodiment of such a digital volume is described below in conjunction with FIG. 4.

Figure 4:
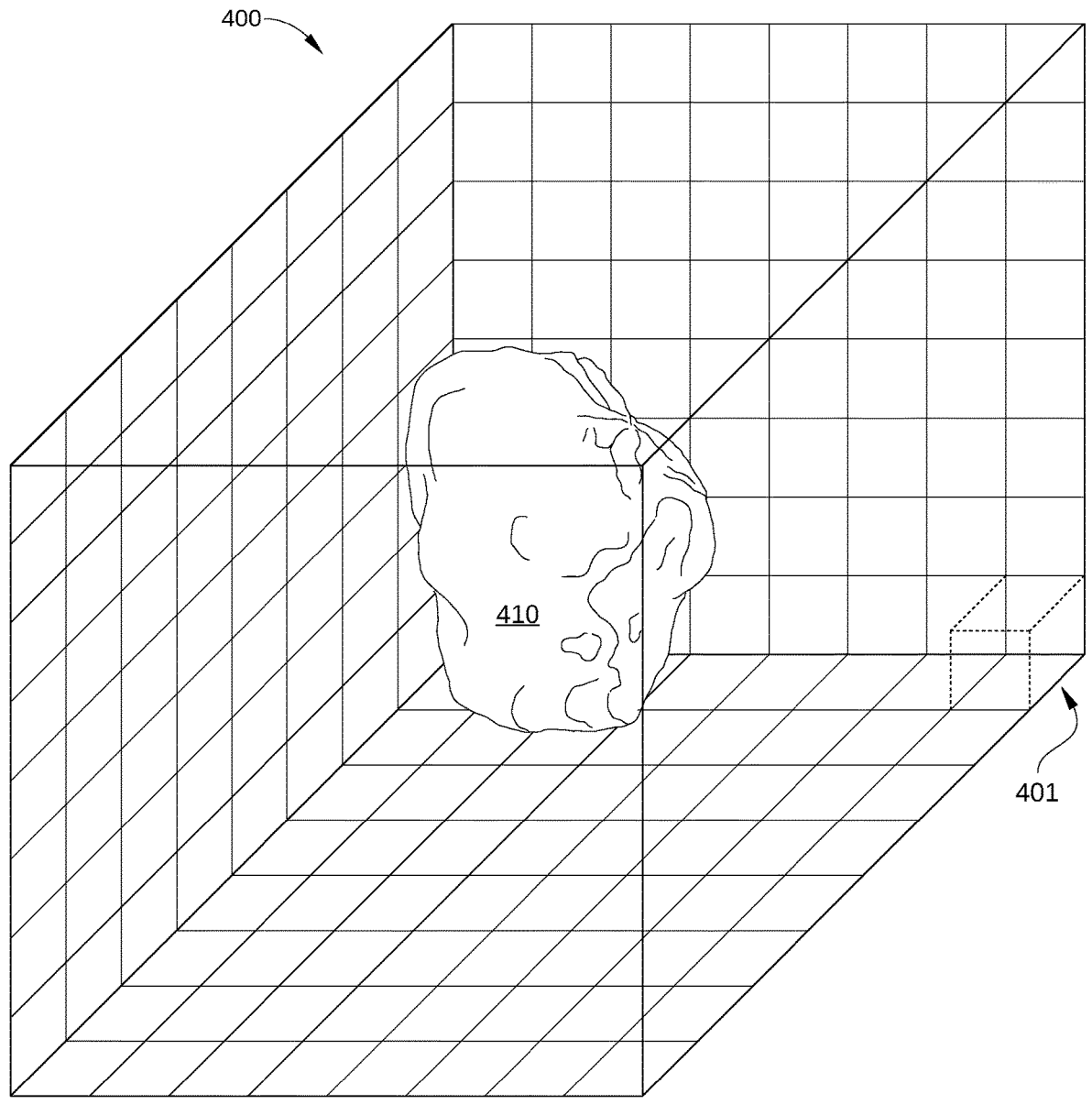
FIG. 4 schematically illustrates a digital volume that is constructed based on projection images generated by one or more X-ray images included in the radiation therapy system of FIG. 1, according to various embodiments.

FIG. 4 schematically illustrates a digital volume 400 that is constructed based on projection images generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for subclinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

In some embodiments, image information associated with each voxel 401 of digital volume 400 is constructed via projection images generated by the single or multiple X-ray imagers via a CBCT process. For example, such a CBCT process can be employed immediately prior to delivering treatment beam 230 to target volume 410, so that the location and shape of target volume 410 can be confirmed before treatment begins.

Calculating Dose Based on a Time-Resolved Machine State and a Time-Resolved Surface of Patient Anatomy According to various embodiments, radiation dose delivered by a radiotherapy system to locations within a digital volume, such as digital volume 400, is calculated based on a time-resolved machine state and a time-resolved surface of patient anatomy. More specifically, a treatment fraction is divided into a plurality of time segments, for example having a duration on the order of a few milliseconds. For each time segment, changes in the location and/or shape of target volume 400 (and in some embodiments OARs) relative to the planning isocenter can be inferred from the time-resolved surface of patient anatomy for that time segment. In this way, for each time segment of a treatment fraction, the effect of such changes in location and/or shape on radiation dose delivered to each location within the digital volume can be calculated and tracked. One such embodiment is described below in conjunction with FIGS. 5-6F.

FIG. 5 sets forth a flowchart of a computer-implemented method 500 for determining radiation dose delivered by a radiotherapy system to a plurality of locations within a region of patient anatomy, according to one or more embodiments. Various steps of computer-implemented method 500 are schematically illustrated in FIGS. 6A, 6B, 6C, 6D, 6E, and 6F, according to various embodiments. In some embodiments, computer-implemented method 500 can be performed as a radiotherapy session or radiotherapy treatment fraction. Generally, radiotherapy treatment fractions are employed to reduce toxic effects on healthy cells, by dividing a total dose of radiation for a patient into multiple smaller doses (fractions). Typically, each treatment fraction is delivered over a period of several or many days, for example every day for several weeks.

Computer-implemented method 500 may include one or more operations, functions, or actions as illustrated by one or more of blocks 501-520. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented method 500 is described in conjunction with RT system 100 and FIGS. 1-4, persons skilled in the art will understand that performance of computer-implemented method 500 by any suitably configured radiotherapy system is within the scope of the present embodiments. For example, in some embodiments, some or all of the operations associated with computer-implemented method 500 can be implemented via image acquisition and treatment control computer 106 and/or remote control console 110 in FIG. 1. Alternatively or additionally, in some embodiments, some or all of the operations associated with computer-implemented method 500 can be implemented via one or more computing devices external to RT system 100. In such embodiments, one or more of the operations associated with computer-implemented method 500 can be performed offline, such as after completion of a radiation therapy fraction and before starting a subsequent radiotherapy treatment fraction.

Figure 6A:
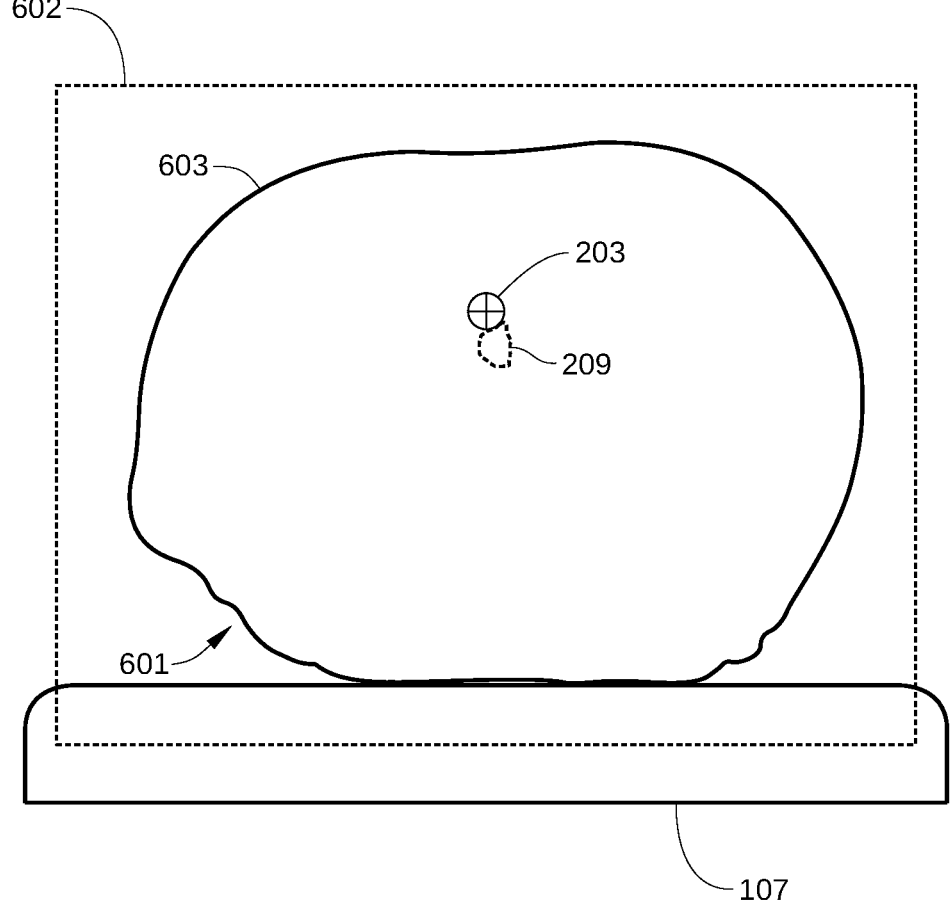
FIGS. 6A, 6B, 6C, 6D, 6E, and 6F illustrate various steps of the computer-implemented method of FIG. 5, according to various embodiments.

In step 501, a patient is positioned within RT system 100 for a radiotherapy treatment fraction, which can be one of multiple treatment fractions planned for the patient. In some embodiments, a patient 601 is positioned on couch 107 so that isocenter 203 of RT system 100 is included in a region of interest 602 of patient anatomy, as shown in FIG. 6A. In some embodiments, tattoos or other skin markings are employed to facilitate positioning of patient 601 relative to RT system 100. Region of interest 602 of patient anatomy, referred hereinafter as "region 602" can be any technically feasible portion of patient anatomy, such as the head, chest, abdomen, and the like, that includes a PTV or other target volume 209. As shown, region 602 includes a surface 603 of patient 601. For clarity, in the embodiment illustrated in FIG. 6A, region 602 is depicted as a 2D cross-section of patient 601. In practice, region 602 is typically a 3D region of patient anatomy. Similarly, in the embodiment illustrated in FIG. 6A, surface 603 is depicted as a 2D outline of patient 601, while in practice surface 603 is typically a 3D surface of some or all of patient 601.

In step 502, pre-treatment imaging of region 602 is performed. In some embodiments, X-ray imaging of region 602 is performed in step 602, for example via an on-board imaging system included in RT system 100. In such embodiments, CBCT X-ray images are acquired using imaging X-ray source 206 and X-ray imager 207 or by a computed tomography (CT) imaging system coupled to or associated with RT system 100. In other embodiments, magnetic resonance imaging (MRI) is performed in step 502, for example via an MRI system coupled to or associated with RT system 100.

Figure 6B:
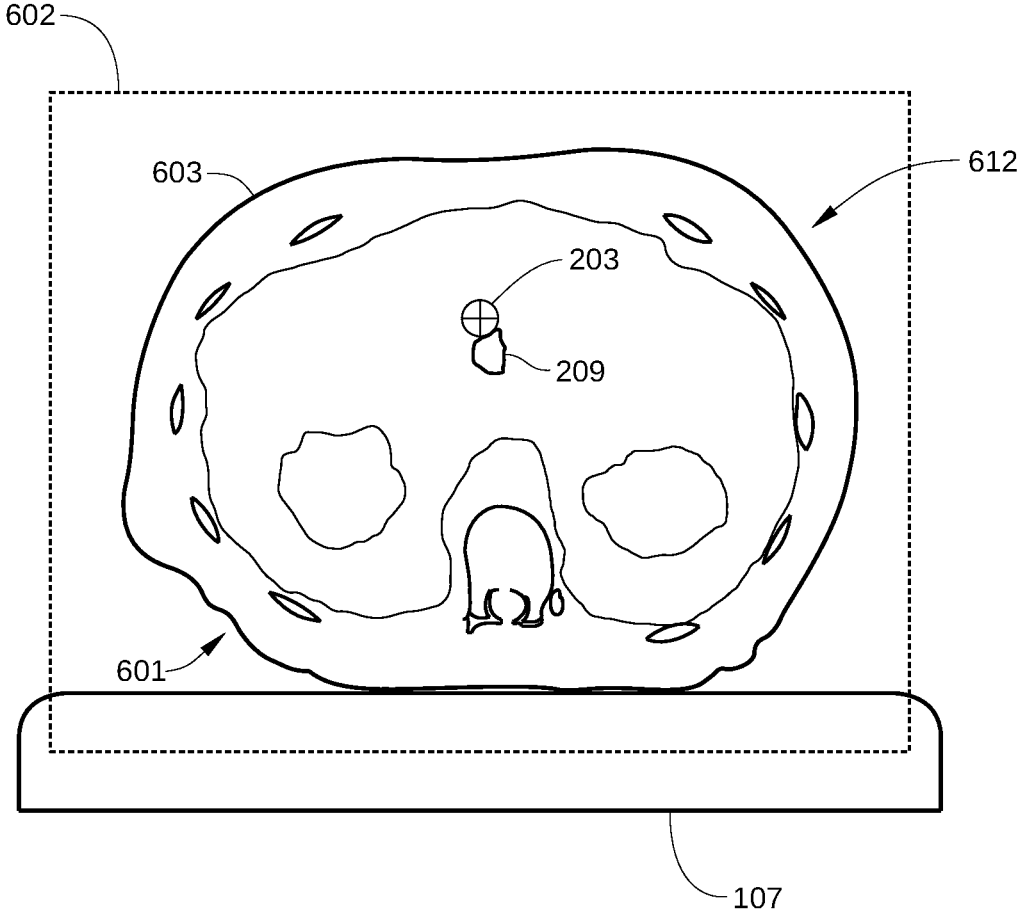

In step 503, a pre-treatment digital volume 612 of region 602 is reconstructed based on the imaging performed in step 502. Pre-treatment digital volume 612 of region 602 is typically a 3D digital volume consistent with digital volume 400 in FIG. 4 and includes target volume 209, as shown in FIG. 6B. In the embodiment illustrated in FIG. 6B, pre-treatment digital volume 612 is depicted relative to couch 107 and isocenter 203. Because pre-treatment digital volume 612 is reconstructed based on the imaging performed in step 502, pre-treatment digital volume 612 indicates the current position of target volume 209 and surface 603 relative to isocenter 203 and components of RT system 100, such as gantry 210 and LINAC 204.

Figure 6C:
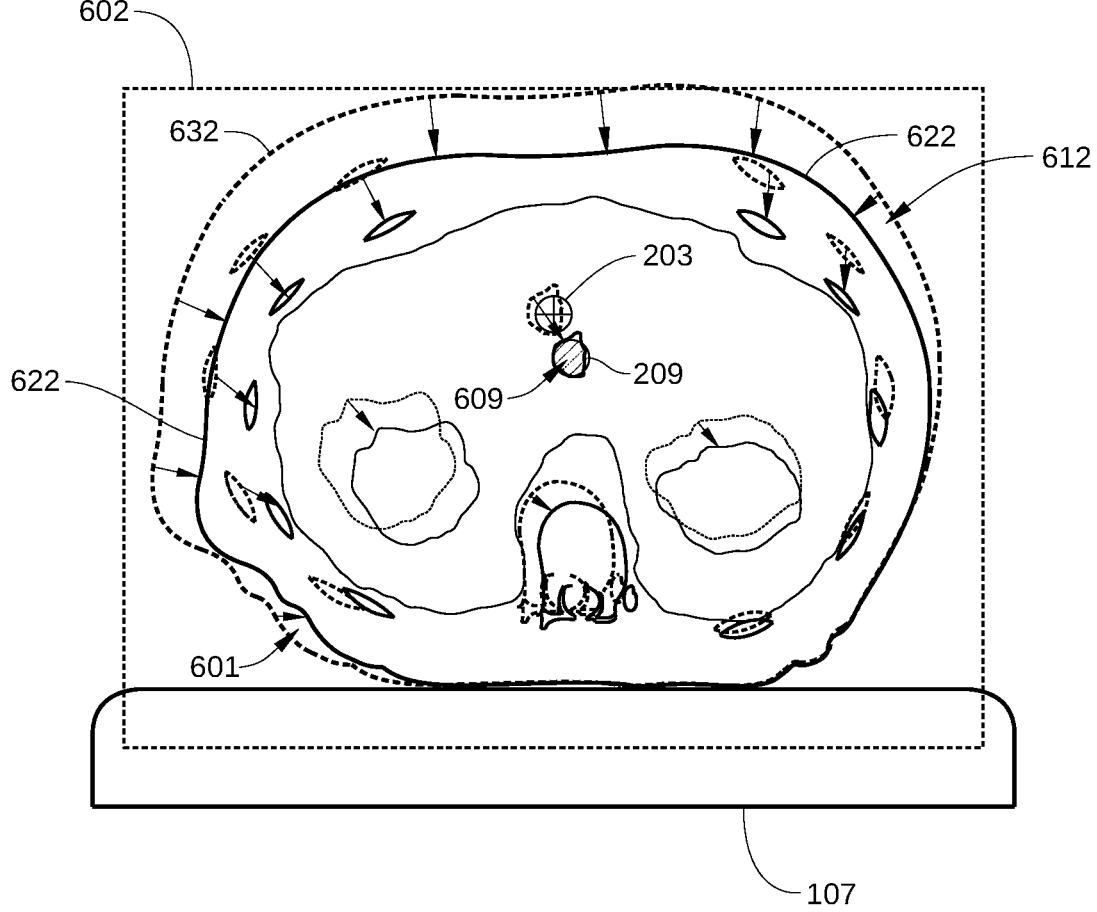

In step 504, a baseline digital volume 622 of region 602 is generated based on the imaging performed in step 502. In some embodiments, baseline digital volume 622 of region 602 is generated by deformably registering a planning digital volume 632 (dashed lines) of region 602 to pre-treatment digital volume 612 of region 602, as shown in FIG. 6C. Typically, planning digital volume 632 of region 602, such as a planning CT image or a CT-quality CBCT image, is acquired prior to computer-implemented method 500. Alternatively, in some embodiments, planning digital volume 632 of region 602 is acquired during computer-implemented method 500, for example via onboard CT-quality CBCT imaging. Deformable image registration accounts for or tracks soft tissue deformation between image acquisitions, and is the process of finding correspondence between the elements of a first 2D image or 3D volume of region 602 (e.g., planning digital volume 632) and the elements of a subsequently acquired second 2D image or 3D volume (e.g., pre-treatment digital volume 612). As is well-known in the art, deformable image registration is designed to find such correspondences that are not the result of simple rigid shifts and/or rotations of region 602 between acquisitions. Various different algorithms have been developed for deformable image registration in radiotherapy applications, including optical and fluid flow, spline-based methods, and biomechanical models. Any suitable deformable registration algorithm can be employed in step 504.

In the embodiment illustrated in FIG. 6C, baseline digital volume 622 accurately indicates the current position of target volume 209 and a planning isocenter 609 (cross-hatched) relative to the current isocenter 203 of RT system 100. Therefore, in step 505, the current position of planning isocenter 609 relative to the current isocenter 203 of RT system 100 can be determined via baseline digital volume 622.

Figure 6D:
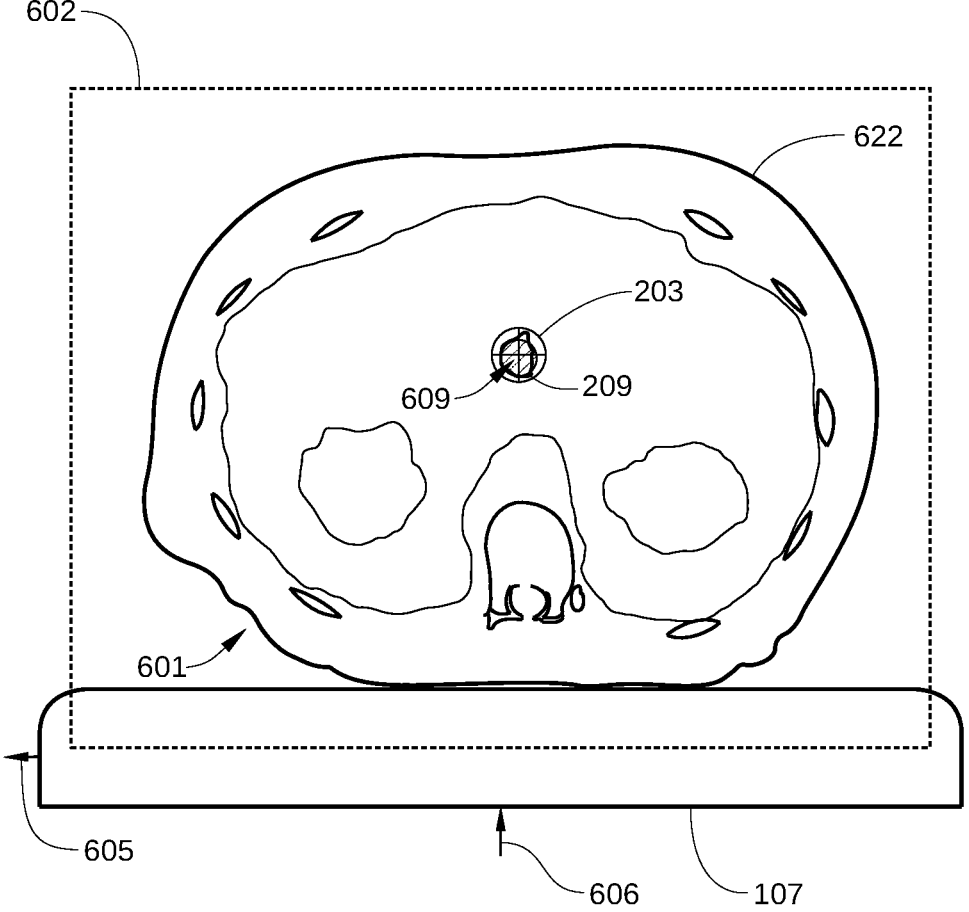

In step 506, the position of couch 107 is changed to shift the location of region 602 relative to the current isocenter 203 of RT system 100, as shown in FIG. 6D. Specifically, couch 107 is repositioned to align planning isocenter 609 with the current isocenter 203 of RT system 100. Ideally, planning isocenter 609 is located at isocenter 203 of RT system 100 during delivery of radiation to facilitate accurate dosing of target volume 209 and to minimize or otherwise reduce dosing to OARs (not shown in FIG. 6D) proximate target volume 209. In the embodiment illustrated in FIG. 6D, couch 107 is repositioned via a vertical shift 605 and a horizontal shift 606 to align planning isocenter 609 with the current isocenter 203. In some embodiments, an axial shift (not shown) into or out of the page may also be employed to align planning isocenter 609 with the current isocenter 203.

In step 507, with planning isocenter 609 aligned with isocenter 203 of RT system 100, the radiotherapy treatment fraction associated with computer-implemented method 500 begins. According to various embodiments, the radiotherapy treatment fraction associated with computer-implemented method 500 is divided into a plurality of time segments, and steps 510-516 are performed for each time segment. In the embodiments, an incremental radiation dose for each such time segment is determined based on a time-segment specific machine state of RT system 100 and a time-segment specific surface of region 602. Thus, in such embodiments, a total radiation dose can be determined based on a time-resolved machine state of RT system 100 and a time-resolved surface of region 602. Because each time segment has a relatively short duration (for example, on the order of a few milliseconds to 10s of milliseconds) the radiation dose determined for each time segment has a high level of temporal granularity, and therefore can accurately quantify the effect on radiation dose caused by intra-fraction patient motion that occurs during a single radiotherapy treatment fraction.

In some embodiments, the time-resolved machine state of RT system 100 includes, for each process parameter associated with RT system 100, a set of values for the radiotherapy treatment fraction associated with computer-implemented method 500. In such embodiments, the set of values for a particular process parameter includes a value of the particular process parameter for each time segment of the radiotherapy treatment fraction. Further, in such embodiments, a process parameter can be any setting or configuration of RT system 100 that effects the location and/or intensity of radiation delivery within region 602 during the radiotherapy treatment fraction, such as gantry rotation, collimator position, beam energy, and the like. Similarly, in some embodiments, the time-resolved surface of region 602 for the radiotherapy treatment fraction includes a set of surface maps of patient anatomy. In such embodiments, each surface map in the set of surface maps of patient anatomy is generated for a different time segment of the radiotherapy treatment fraction, as described below.

In step 510, the radiotherapy treatment fraction associated with computer-implemented method 500 increments to the next time segment. In step 511, radiotherapy for the current time segment of the radiotherapy treatment fraction is performed. Thus, radiation is delivered to target volume 209 while RT system 100 is configured in a particular machine state. For example, in some embodiments, the machine state includes a current value for each process parameter associated with RT system 100 that effects the location and intensity of radiation delivery within region 602 during the current time segment. Consequently, in some embodiments, the machine state includes information indicating the current position or setting of each machine axis associated with RT system 100, such as for couch 107, gantry 210, one or more collimators associated with LINAC 204, individual leaf positions of a multi-leaf collimator associated with LINAC 204, power, and/or other operational settings for LINAC 204 and/or treatment beam 230. Thus, the machine state of RT system 100 provides a snapshot of what RT system 100 is doing during the current time segment of the radiotherapy treatment fraction. Generally, the specific process parameters referenced by the machine state can vary depending on the specific configuration of RT system 100, i.e., these specific process parameters are system-dependent.

In step 512, the machine state of RT system 100 in the current time segment is stored. For example, in some embodiments, a system log file is updated to include the values for each process parameter associated with RT system 100 during the current time segment.

Figure 6E:
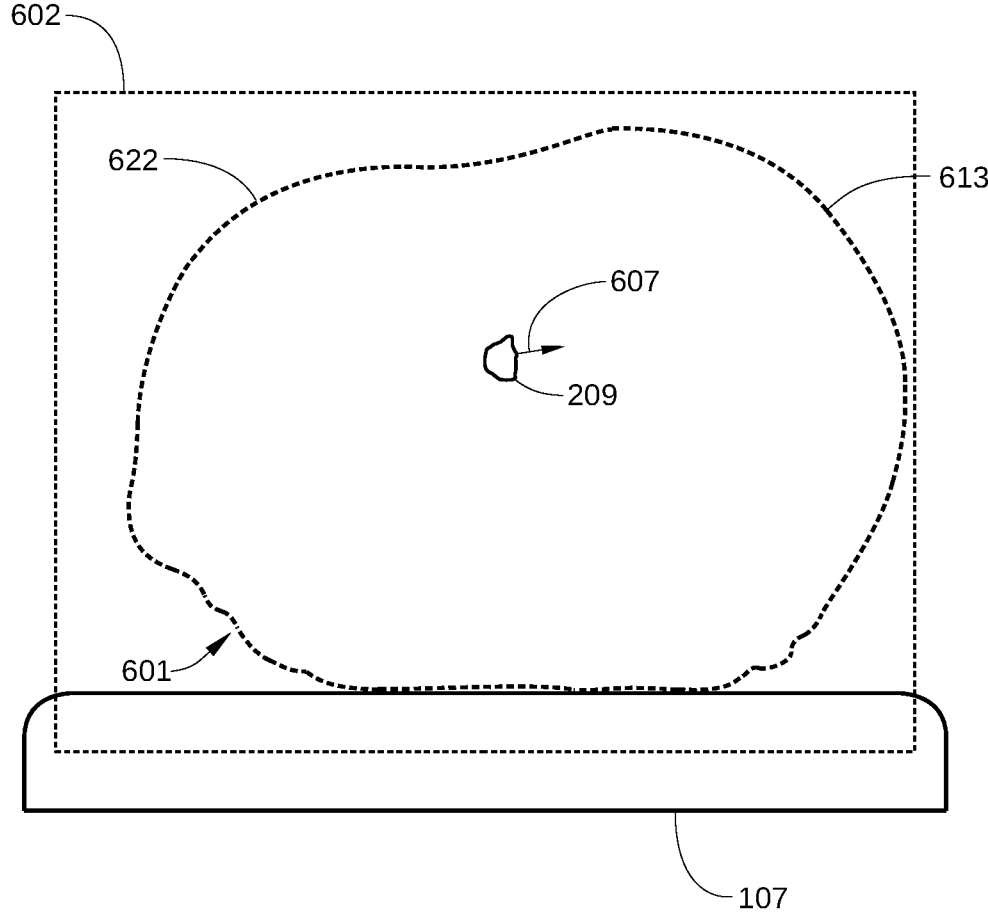

In step 513, a surface map of patient anatomy is generated for the current time segment of the radiotherapy treatment fraction. In some embodiments, a surface map is generated that indicates a current surface 613 of patient 601 relative to isocenter 203 of RT system 100, as shown in FIG. 6E. In the embodiment illustrated in FIG. 6E, current surface 613 is depicted as a 2D outline of region 602, but in practice current surface 613 is typically a 3D surface. In some embodiments, current surface 613 is generated for a surface associated with region 602 of patient anatomy. In other embodiments, current surface 613 is generated for a surface associated with most or all of the anatomy of patient 601. In either case, the surface map of current surface 613 is generated based on surface measurements acquired during the current time segment of the radiotherapy treatment fraction, for example via one or more patient-monitoring sensors 109 and an associated patient position-monitoring system or surface image guidance system.

In FIG. 6E, intra-fraction motion of some or all portions of the anatomy associated with region 602 has caused current surface 613 to deviate from a surface 623 of baseline digital volume 622. Such intra-fraction motion can be caused by voluntary movement by the patient, such as the breathing, coughing, contraction of skeletal muscles, and the like. In addition, such intra-fraction motion can be caused by involuntary movement, such as organs affected by peristalsis, gas motion, and the like. In addition to the deviation of current surface 613 from surface 623 of baseline digital volume 622, intra-fraction motion also causes anatomical structures within region 602 to be displaced from their assumed positions. For example, intra-fraction motion can cause target volume 209 and/or one or more OARs (not shown) to undergo a change in position 607 or shape within region 602, which directly affects dose delivered thereto. As a result, during the current time segment, target volume 209 may receive less dose than planned and healthy tissue proximate target volume 209 may receive more dose than anticipated.

Figure 6F:
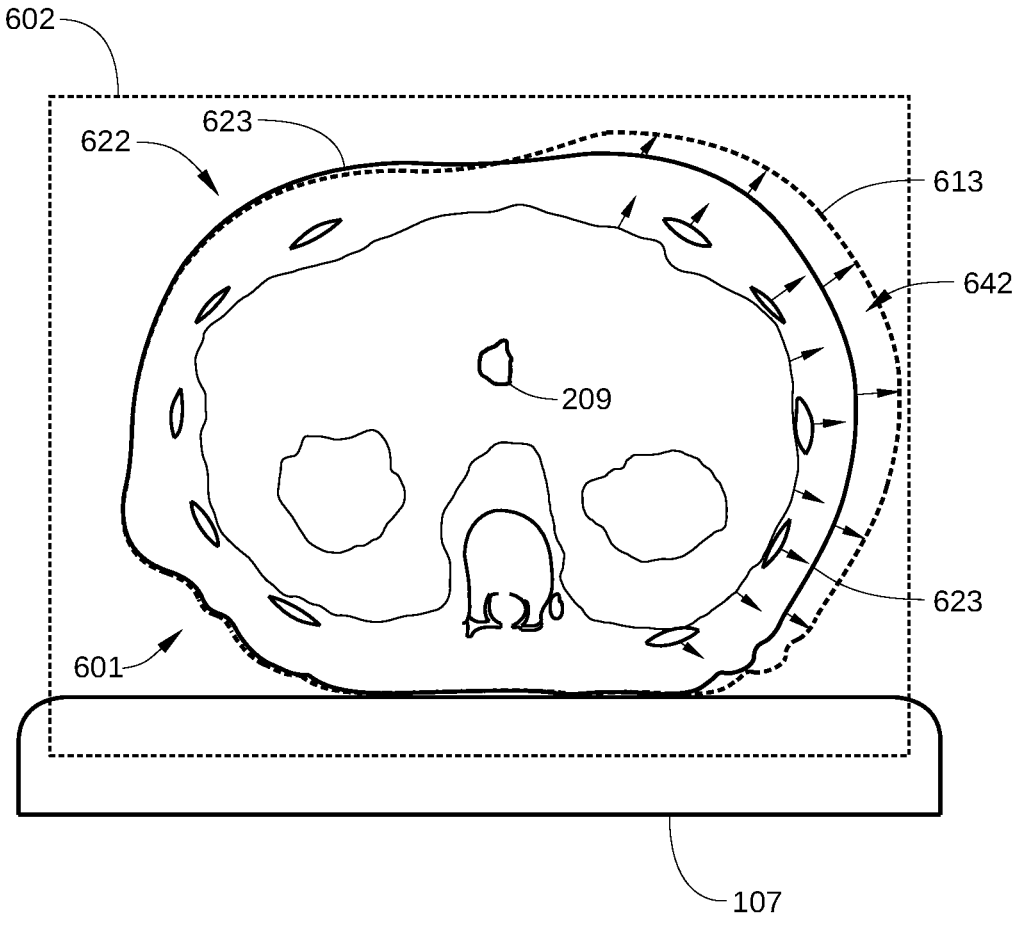

In step 514, a modified digital volume 642 of region 602 is generated incorporating the deformation of region 602 that is indicated by current surface 613. In some embodiments, modified digital volume 642 is generated by deformably registering surface 623 of baseline digital volume 622 to current surface 613, as shown in FIG. 6F. It is noted that surface 623 of baseline digital volume 622 corresponds to the surface of patient 601 at the time that pre-treatment imaging of region 602 is performed in step 502. Alternatively, in some embodiments, modified digital volume 642 is generated by deformably registering a body outline of patient 601 to current surface 613. In such embodiments, the body outline of patient 601 is based on imaging acquired in step 502 via pre-treatment imaging of region 602. In either case, the actual position of target volume 209, OARs within region 602, bony structures, and other anatomical structures relative to isocenter 203 are indicated by modified digital volume 642. As a result, the actual incremental dose delivered to target volume 209 and OARs and other locations within region 602 can be determined for the current time segment. Any suitable deformable registration algorithm can be employed in step 514.

It is noted that delivered dose to a particular anatomical structure can be significantly affected by changes in position of that particular anatomical structure from the planned location of that anatomical structure. For example, intra-fraction motion during a particular time segment may result in target volume 209 being displaced from isocenter 203 and therefore receiving a different dose than planned. Similarly, delivered dose to a particular anatomical structure can be significantly affected by changes in position of other anatomical structures, such as high-radiodensity structures that can block a greater portion of treatment beam 230. For example, intra-fraction motion during a particular time segment may cause a bony structure to be unexpectedly positioned between target volume 209 and LINAC 204, thereby decreasing the planned dose to target volume 209 during that particular time segment.

In step 515, an incremental radiation dose is determined for each location within region 602. In some embodiments, the incremental radiation dose for each location within region 602 is determined based on modified digital volume 642 of region 602 and on the machine state of RT system 100 for the current time segment. In such embodiments, an incremental radiation dose for each voxel 401 within modified digital volume 642 can be determined. Because modified digital volume 642 indicates the actual position of target volume 209, OARs within region 602, bony structures, and other anatomical structures relative to isocenter 203, the incremental radiation dose for each voxel 401 within modified digital volume 642 accurately reflects radiation dose delivered to such locations within region 602.

In step 515, any technically feasible algorithm can be employed to determine the incremental radiation dose for each location within region 602. Various algorithms are known in the art for calculating 3D delivered dose in a region of patient anatomy based on a digital volume of the region and on values for the various treatment parameters. Thus, any such algorithm can be employed in step 515. In some embodiments, such an algorithm can be implemented via image acquisition and treatment control computer 106 and/or remote control console 110. In other embodiments, a computing device external to RT system 100 can implement such an algorithm in step 515.

In step 516, the determination is made whether the radiotherapy treatment fraction is complete. If no, computer-implemented method 500 returns to step 510 and increments to the next time segment of the radiotherapy treatment fraction; if yes, computer-implemented method 500 proceeds to step 520.

In step 520, for each location within region 602, a total radiation dose delivered during the radiotherapy treatment fraction is determined, where the total radiation dose is based on the sum of the incremental radiation doses calculated in each iteration of step 515. As described above, each iteration of step 515 is associated with a different time segment of the radiotherapy treatment fraction. In some embodiments, the total radiation dose for a particular location is determined by accumulating the incremental radiation dose for each time segment in planning digital volume 632 for that particular location. However, the incremental dose for each time segment is determined based on a specific modified digital volume 642 for that time segment, and specific modified digital volume 642 can reflect changes in shape of anatomy in region 602 caused by intra-fraction motion. Consequently, in such embodiments, to accumulate an incremental dose associated with a particular time segment in planning digital volume 632, the modified digital volume 642 associated with that particular time segment is deformably registered to planning digital volume 632. In this way, the plurality of incremental radiation doses that are received by the differently shaped modified digital volumes 642 can be accurately accumulated in a reference digital volume for quality assurance analysis. As noted above, planning digital volume 632 can be a conventional CT image, a CT-quality CBCT image, or the like.

In the embodiments described above, steps 514 and 515 are performed during each time segment of the radiotherapy treatment fraction. In other embodiments, steps 514 and 515 are performed after the radiotherapy treatment fraction has been completed.

Use of Time-Resolved Radiation Dose for Quality Assurance

In light of the above, time-resolved (or incremental) radiation doses delivered to locations within a digital volume can be used to accurately determine the total radiation dose delivered in a radiotherapy treatment fraction for each location within the digital volume. Because the incremental radiation doses are calculated based on a time-resolved machine state and a time-resolved surface of patient anatomy, the effect of intra-fraction motion on radiation dose delivered to each location within the digital volume can be taken into account when calculating dose delivered. According to various embodiments, based on a dose error detected after a radiotherapy treatment fraction, one or more subsequent radiotherapy treatment fractions are modified to compensate for the detected dose error. One such embodiment is described below in conjunction with FIG. 7.

Figure 7:
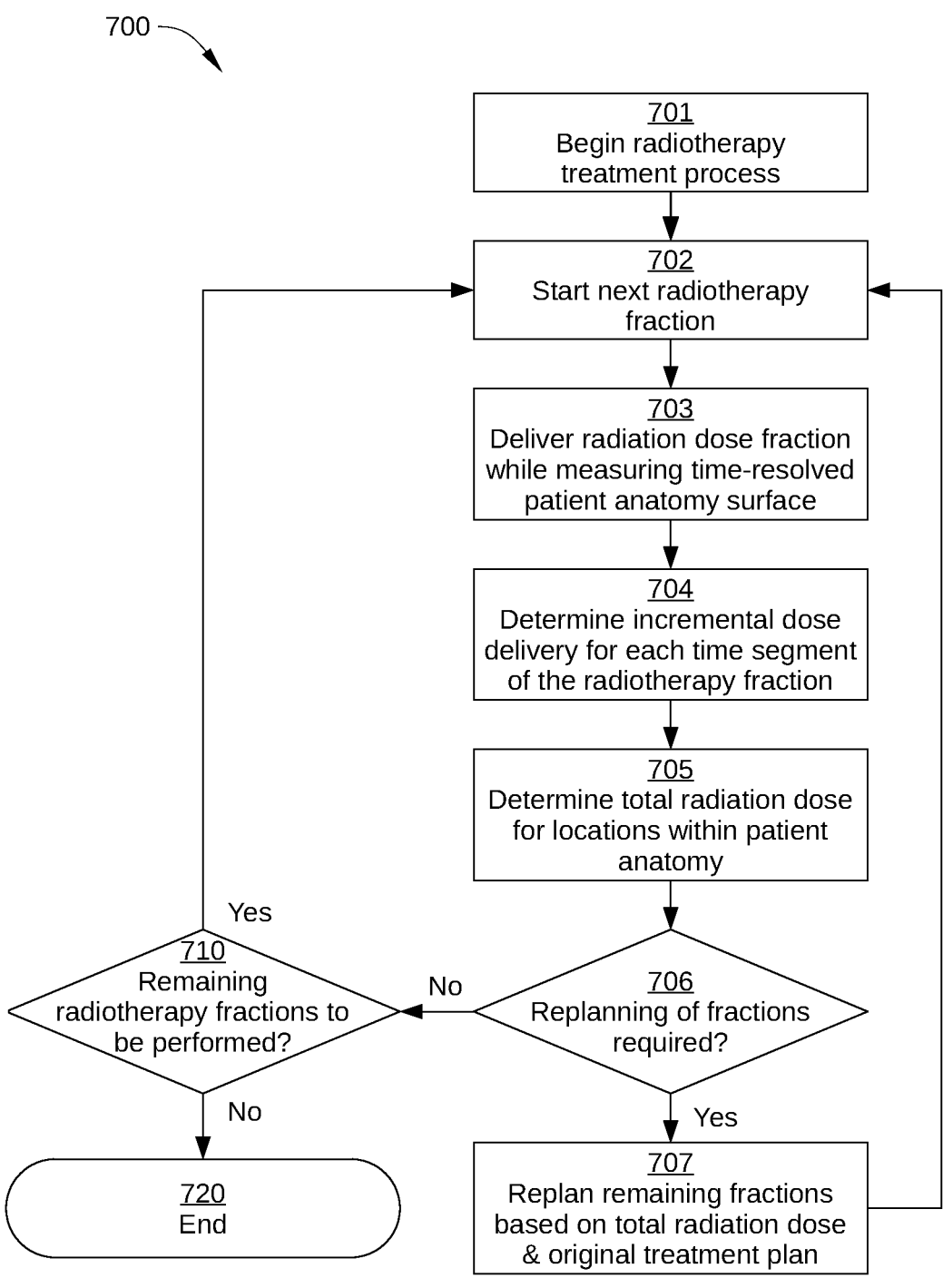
FIG. 7 sets forth a flowchart of a computer-implemented method 700 of radiotherapy for a region of patient anatomy, according to one or more embodiments.

FIG. 7 sets forth a flowchart of a computer-implemented method 700 of radiotherapy for a region of patient anatomy, according to one or more embodiments. In some embodiments, computer-implemented method 700 can be performed as a radiotherapy process that includes a plurality of radiotherapy treatment fractions. Typically, each treatment fraction is delivered over a period of several or many days, for example every day for several weeks.

Computer-implemented method 700 may include one or more operations, functions, or actions as illustrated by one or more of blocks 701-720. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented method 700 is described in conjunction with RT system 100 and FIGS. 1-4, persons skilled in the art will understand that performance of computer-implemented method 700 by any suitably configured radiotherapy system is within the scope of the present embodiments. For example, in some embodiments, some or all of the operations associated with computer-implemented method 700 can be implemented via image acquisition and treatment control computer 106 and/or remote control console 110 in FIG. 1. Alternatively or additionally, in some embodiments, some or all of the operations associated with computer-implemented method 700 can be implemented via one or more computing devices external to RT system 100.

In step 701, a radiotherapy treatment process that includes multiple radiotherapy treatment fractions begins. In some embodiments, the radiotherapy treatment process is planned based on a planning CT or other imaging. In some embodiments, for the radiotherapy treatment process, there is a target minimum dose to be delivered for a target volume 209 and a maximum allowable dose for one or more OARs or other anatomical structures. Additionally or alternatively, in some embodiments, for each radiotherapy treatment fraction, there is a target minimum dose to be delivered for a target volume 209 and a maximum allowable dose for one or more OARs or other anatomical structures.

In step 702, the next radiotherapy treatment fraction begins. For example, in some embodiments, operations consistent with steps 501-507 of FIG. 5 are performed. In step 703, the radiation dose for the current radiotherapy treatment fraction is delivered while a time-segment specific surface of region 602 is measured or acquired. For example, in some embodiments, operations consistent with steps 510-513 of FIG. 5 are performed.

In step 704, an incremental dose delivery for each time segment of the current radiotherapy treatment fraction is determined. For example, in some embodiments, operations consistent with steps 514 and 515 of FIG. 5 are performed. In such embodiments, the incremental dose delivery for a plurality of locations within region 602 is determined for each time segment of the current radiotherapy treatment fraction.

In step 705, for each location within region 602, a total radiation dose delivered during the radiotherapy treatment fraction is determined, where the total radiation dose is based on the sum of the incremental radiation doses calculated in step 704. For example, in some embodiments, operations consistent with step 520 of FIG. 5 are performed.

In step 706, the determination is made whether replanning of remaining radiotherapy treatment fractions is required. For example, in some embodiments, replanning of remaining fractions is required when a target minimum dose to be delivered for a target volume 209 is not achieved by the just-completed radiotherapy treatment fraction. Thus, additional dose is to be planned for target volume 209 to compensate for this detected dose error. In such embodiments, the target minimum dose can indicate a threshold value for the just-completed radiotherapy treatment fraction or a threshold value for all completed radiotherapy treatment fractions (i.e., a running threshold value that increases with each completed radiotherapy treatment fraction). In another example, in some embodiments, replanning of remaining fractions is required when a maximum allowable dose to be delivered to one or more OARs is exceeded by the just-completed radiotherapy treatment fraction. Thus, less dose is to be planned in subsequent radiotherapy treatment fractions for the one or more OARs to compensate for the excessive dose detected in the earlier radiotherapy treatment fraction(s). In such embodiments, the maximum allowable dose can indicate a maximum allowable dose value for the just-completed radiotherapy treatment fraction or a maximum allowable dose value for all completed radiotherapy treatment fractions (i.e., a running maximum allowable dose value that increases with each completed radiotherapy treatment fraction). If the determination is made that no replanning of remaining fractions is required, computer-implemented method 700 proceeds to step 710. If the determination is made that replanning of remaining fractions is required, computer-implemented method 700 proceeds to step 707.

In step 707, one or more remaining fractions of the radiotherapy process associated with computer-implemented method 700 are replanned to compensate for the dose error (or other failure to achieve a dosimetric goal) that is detected in step 706. In step 707, the replanning is based on an original treatment plan and on the total radiation dose for locations within region 602 determined in step 705. In some embodiments, replanning of a treatment plan includes changing the time-resolved machine state for RT system 100 from a previously planned machine state to a new state. In the new state, one or more process parameter values included in the planned machine state is changed. Given a replanned target dose for each location within region 602, one of skill in the art can employ any suitable treatment planning algorithm to perform step 707. Computer-implemented method 700 then returns to step 702 and the next radiotherapy treatment fraction is performed.

In step 710, the determination is made whether there are any remaining radiotherapy treatment fractions to be performed in the radiotherapy process associated with computer-implemented method 700. If yes, computer-implemented method 700 returns to step 702 and the next radiotherapy treatment fraction is performed; if no, computer-implemented method 700 proceeds to step 720 and terminates.

Use of Time-Resolved Radiation Dose for Adaptive Radiotherapy

In some embodiments, accumulated, time-resolved radiation doses that are delivered to locations within a digital volume can be used to detect deviation of dose delivery during a particular radiotherapy treatment fraction. In such embodiments, the radiation dose delivered in a remaining portion of the radiotherapy treatment fraction can be replanned to compensate for the detected deviation of dose in the portion of the radiotherapy treatment fraction that has already been performed. As a result, the total radiation dose delivered upon completion of the radiotherapy treatment fraction can be free of dose error or have a reduced dose error. One such embodiment is described below in conjunction with FIG. 8.

Figure 8:
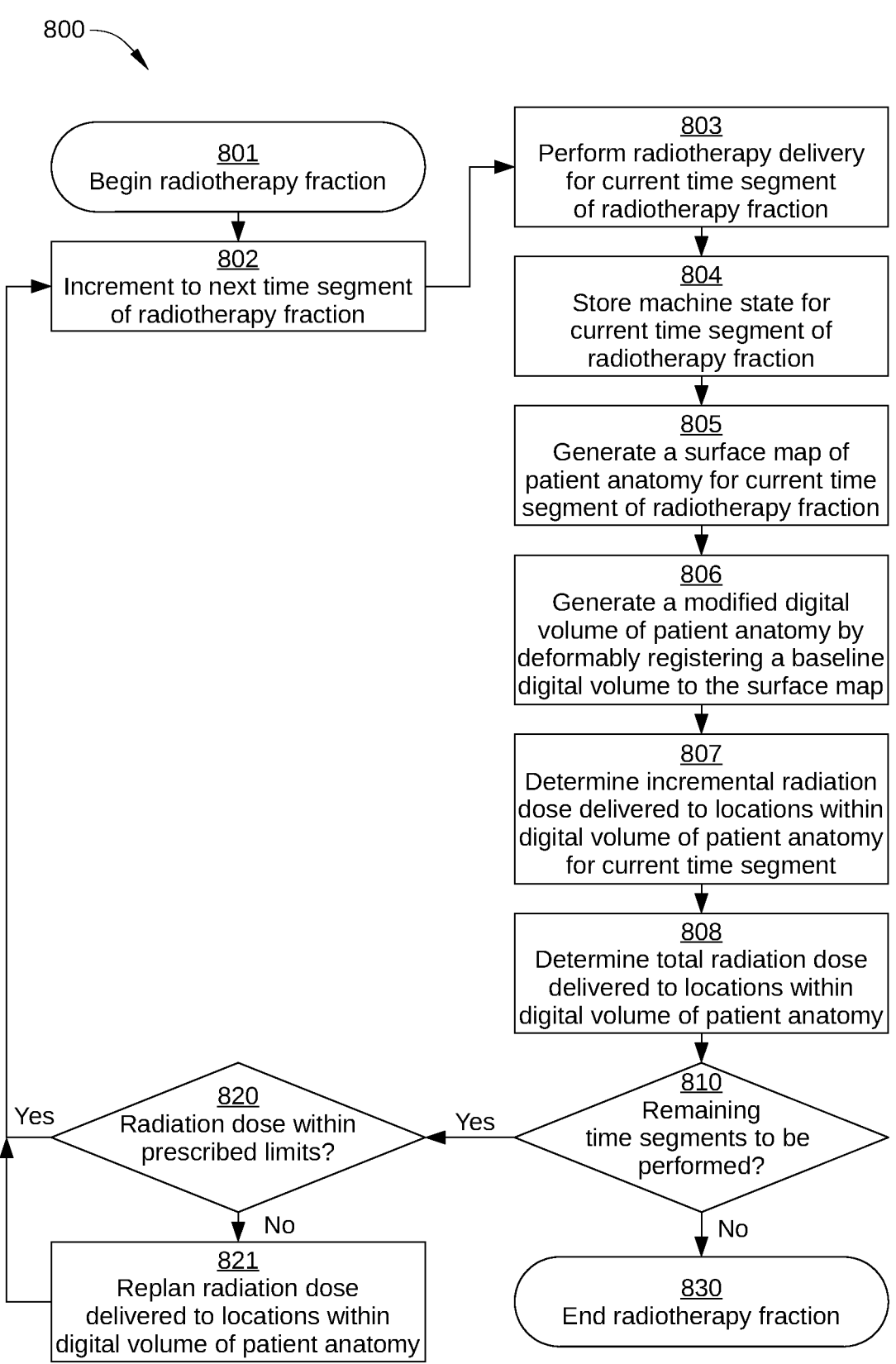
FIG. 8 sets forth a flowchart of a computer-implemented method 800 of radiotherapy for a region of patient anatomy, according to one or more embodiments.

FIG. 8 sets forth a flowchart of a computer-implemented method 800 of radiotherapy for a region of patient anatomy, according to one or more embodiments. In some embodiments, computer-implemented method 800 can be performed as a radiotherapy treatment fraction. Generally, a radiotherapy process includes a plurality of such radiotherapy treatment fractions, where each treatment fraction is delivered over a period of several or many days, for example every day for several weeks.

Computer-implemented method 800 may include one or more operations, functions, or actions as illustrated by one or more of blocks 801-821. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented method 800 is described in conjunction with RT system 100 and FIGS. 1-4, persons skilled in the art will understand that performance of computer-implemented method 800 by any suitably configured radiotherapy system is within the scope of the present embodiments. For example, in some embodiments, some or all of the operations associated with computer-implemented method 800 can be implemented via image acquisition and treatment control computer 106 and/or remote control console 110 in FIG. 1. Alternatively or additionally, in some embodiments, some or all of the operations associated with computer-implemented method 800 can be implemented via one or more computing devices external to RT system 100.

In step 801, a radiotherapy treatment fraction that includes a plurality of time segments begins. For example, in some embodiments, the radiotherapy treatment fraction is planned based on a planning CT or other imaging and includes a series of hundreds or thousands of time segments. In some embodiments, for each time segment of the radiotherapy treatment fraction, there is a target minimum dose to be delivered for a target volume 209 and a maximum allowable dose for one or more OARs or other anatomical structures. In some embodiments, operations consistent with steps 501-507 of FIG. 5 are performed in step 801. In step 802, the radiotherapy treatment fraction associated with computer-implemented method 800 increments to the next time segment.

In step 803, radiotherapy for the current time segment of the radiotherapy treatment fraction is performed. Thus, radiation is delivered to target volume 209 while RT system 100 is configured in a particular time segment-specific machine state. In some embodiments, operations consistent with step 511 of FIG. 5 are performed.

In step 804, the time-segment-specific machine state of RT system 100 in the current time segment is stored. In some embodiments, operations consistent with step 512 of FIG. 5 are performed.

In step 805, a surface map of patient anatomy is generated for the current time segment of the radiotherapy treatment fraction. In some embodiments, operations consistent with step 513 of FIG. 5 are performed.

In step 806, a modified digital volume 642 of region 602 is generated incorporating the deformation of region 602 that is indicated by current surface 613. In some embodiments, operations consistent with step 514 of FIG. 5 are performed.

In step 807, an incremental radiation dose is determined for each location within region 602. In some embodiments, operations consistent with step 515 of FIG. 5 are performed.

In step 808, for each location within region 602, a total radiation dose delivered during the radiotherapy treatment fraction is determined, where the total radiation dose is based on the sum of the incremental radiation doses calculated in each iteration of step 807. In some embodiments, operations consistent with step 520 of FIG. 5 are performed.

In step 810, the determination is made whether there are any remaining time segments to be performed in the radiotherapy treatment fraction. If yes, computer-implemented method 800 proceeds to step 820; if no, computer-implemented method 800 proceeds to step 830 and terminates.

In step 820, the determination is made whether the radiation dose for all locations within region 602 are within prescribed limits and replanning of the remaining portion of the radiotherapy treatment fraction is not required. In some embodiments, operations consistent with step 706 of FIG. 7 are performed in step 821. If the determination is made that the radiation dose for all locations within region 602 are within prescribed limits, computer-implemented method 800 returns to step 802 and increments to the next time segment of the radiotherapy treatment fraction. If the determination is made that the radiation dose for one or more locations within region 602 are not within prescribed limits and replanning of the remaining portion of the radiotherapy treatment fraction is required, computer-implemented method 800 proceeds to step 821.

In step 821, one or more remaining time segments of the radiotherapy process associated with computer-implemented method 800 are replanned to compensate for the dose error detected in step 820. In some embodiments, operations consistent with step 707 of FIG. 7 are performed. Computer-implemented method 800 then returns to step 802 and the next time segment of the radiotherapy treatment fraction is performed.

In the embodiment of computer-implemented method 800 described above, replanning of radiation dose delivered to locations within region 602 is performed for each time segment of the radiotherapy treatment fraction. In other embodiments, such replanning of radiation dose to be delivered is performed periodically, such as once every few three, five, or ten time segments. In such embodiments, less computational resources during the radiotherapy treatment fraction are required to perform such replanning.

Example Computing Device

Figure 9:
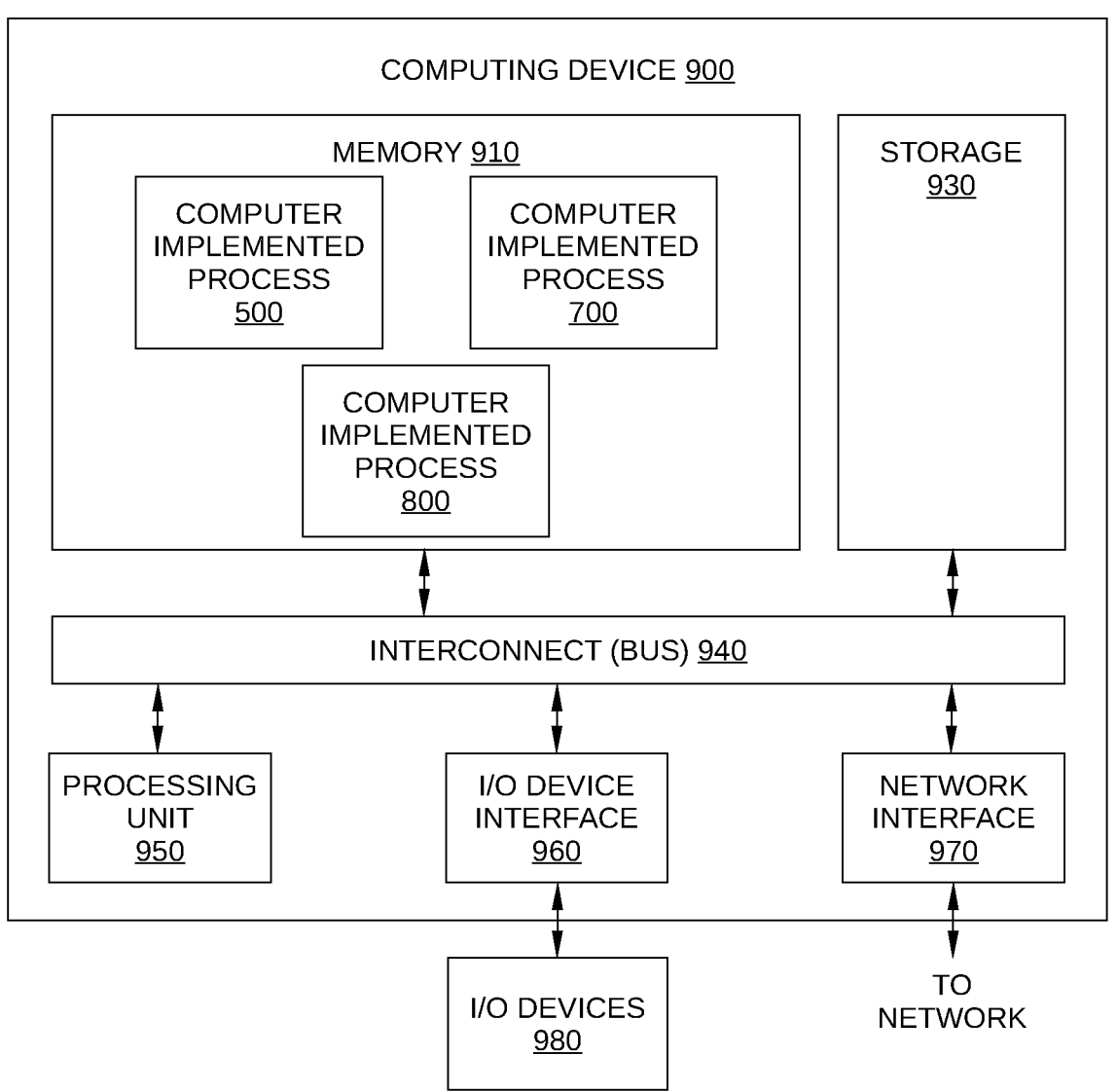
FIG. 9 is an illustration of a computing device configured to perform various embodiments.

FIG. 9 is an illustration of computing device 900 configured to perform various embodiments described herein. For example, in some embodiments, computing device 900 can be implemented as image acquisition and treatment control computer 106 and/or remote control console 110 in FIG. 1. Computing device 900 may be a desktop computer, a laptop computer, a smart phone, or any other type of computing device suitable for practicing one or more embodiments of the present disclosure. In operation, computing device 900 is configured to execute instructions associated with computer-implemented process 900, as described herein. It is noted that the computing device described herein is illustrative and that any other technically feasible configurations fall within the scope of the present disclosure.

As shown, computing device 900 includes, without limitation, an interconnect (bus) 940 that connects a processing unit 950, an input/output (I/O) device interface 960 coupled to input/output (I/O) devices 980, memory 910, a storage 930, and a network interface 970. Processing unit 950 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 950 may be any technically feasible hardware unit capable of processing data and/or executing software applications, including computer-implemented process 500, computer-implemented process 700, and/or computer-implemented process 800.

I/O devices 980 may include devices capable of providing input, such as a keyboard, a mouse, a touch-sensitive screen, and so forth, as well as devices capable of providing output, such as a display device and the like. Additionally, I/O devices 980 may include devices capable of both receiving input and providing output, such as a touchscreen, a universal serial bus (USB) port, and so forth. I/O devices 980 may be configured to receive various types of input from an end-user of computing device 900, and to also provide various types of output to the end-user of computing device 900, such as displayed digital images or digital videos. In some embodiments, one or more of I/O devices 980 are configured to couple computing device 900 to a network.

Memory 910 may include a random access memory (RAM) module, a flash memory unit, or any other type of memory unit or combination thereof. Processing unit 950, I/O device interface 960, and network interface 970 are configured to read data from and write data to memory 910. Memory 910 includes various software programs that can be executed by processor 950 and application data associated with said software programs, including computer-implemented process 500, computer-implemented process 700, and/or computer-implemented process 800.

Example Computer Program Product

Figure 10:
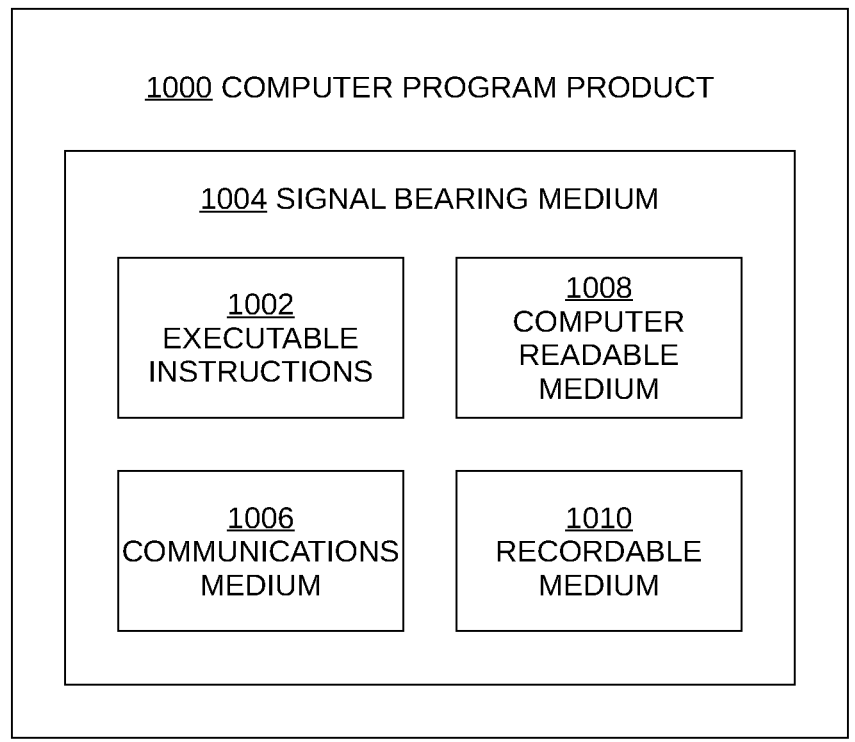
FIG. 10 is a block diagram of an illustrative embodiment of a computer program product for implementing one or more embodiments.

FIG. 10 is a block diagram of an illustrative embodiment of a computer program product 1000 for implementing a method for reducing scatter in an X-ray projection image, according to various embodiments. Computer program product 1000 may include a signal bearing medium 1004. Signal bearing medium 1004 may include one or more sets of executable instructions 1002 that, when executed by, for example, a processor of a computing device, may provide at least the functionality described above with respect to FIGS. 1-8.

In some implementations, signal bearing medium 1004 may encompass a non-transitory computer readable medium 1008, such as, but not limited to, a hard disk drive, a Compact Disc (CD), a Digital Video Disk (DVD), a digital tape, memory, etc. In some implementations, signal bearing medium 1004 may encompass a recordable medium 1010, such as, but not limited to, memory, read/write (R/W) CDs, R/W DVDs, etc. In some implementations, signal bearing medium 1004 may encompass a communications medium 1006, such as, but not limited to, a digital and/or an analog communication medium (e.g., a fiber optic cable, a waveguide, a wired communications link, a wireless communication link, etc.). Computer program product 1000 may be recorded on non-transitory computer readable medium 1008 or another similar recordable medium 1010.

In sum, embodiments described herein enable accurate determination of accumulated radiation dose even when significant intra-fraction motion of patient anatomy occurs during a radiotherapy treatment fraction. When the radiation dose during a radiotherapy treatment fraction deviates from dosimetric goals, subsequent fractions can be replanned to compensate. Consequently, coverage of a target volume and sparing of OARs is facilitated.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A computer-implemented method of determining dose delivered by a radiotherapy system to a plurality of locations within a region of patient anatomy, the method comprising:

during a first time segment of a treatment fraction, causing the radiotherapy system to be in a first machine state, wherein the first time segment has a duration on the order of a few milliseconds to tens of milliseconds;

during the first time segment, delivering radiation to the region of patient anatomy;

generating a first surface map for the region of patient anatomy based on surface measurements acquired during the first time segment;

generating a first modified digital volume of the region based on the first surface map; and for each of the plurality of locations within the region of patient anatomy, determining a first radiation dose that is delivered to the location during the first time segment, wherein the first radiation dose is based on the first machine state of the radiotherapy system and the first modified digital volume.

2. The computer-implemented method of claim 1, wherein generating the first modified digital volume of the region comprises deformably registering a baseline digital volume of the region to the first surface map.

3. The computer-implemented method of claim 2, further comprising:

acquiring imaging of the region; and reconstructing the baseline digital volume based on the imaging.

4. The computer-implemented method of claim 3, wherein the imaging is acquired prior to the treatment fraction.

5. The computer-implemented method of claim 3, wherein the imaging is acquired during the treatment fraction.

6. The computer-implemented method of claim 3, wherein the imaging comprises one of cone-beam computed tomography (CBCT) imaging, magnetic resonance imaging, or computed tomography imaging.

7. The computer-implemented method of claim 1, wherein generating the first modified digital volume of the region comprises deformably registering the first surface map to a baseline digital volume of the region.

8. The computer-implemented method of claim 1, further comprising, for each of the plurality of locations within the region of patient anatomy, determining a second radiation dose that is delivered to the location during a second time segment of the treatment fraction.

9. The computer-implemented method of claim 8, wherein the second radiation dose is based on a second machine state of the radiotherapy system and a second modified digital volume of the region.

10. The computer-implemented method of claim 9, further comprising generating the second modified digital volume of the region by deformably registering a baseline digital volume of the region to a second surface map.

11. The computer-implemented method of claim 9, wherein the second modified digital volume of the region is based on a second surface map for the region of patient anatomy that is based on surface measurements acquired during the second time segment.

12. The computer-implemented method of claim 1, further comprising, for each of the plurality of locations within the region of patient anatomy, determining a total radiation dose that is delivered to the location during the treatment fraction.

13. The computer-implemented method of claim 12, further comprising, for each of the plurality of locations within the region of patient anatomy, determining a second radiation dose that is delivered to the location during a second time segment of the treatment fraction, wherein the total radiation dose that is delivered to the location during the treatment fraction is based on the first radiation dose that is delivered to the location during the first time segment and the second radiation dose that is delivered to the location during the second time segment.

14. A computer-implemented method of radiotherapy for a plurality of locations within a region of patient anatomy, the method comprising:

determining a first total radiation dose that is delivered during a first treatment fraction to a first location included in the plurality of locations, wherein the first total radiation dose is based on a first time-resolved machine state of a radiotherapy system associated with the first treatment fraction, a time-resolved surface map of the region associated with the first treatment fraction, and the first treatment fraction includes a plurality of time segments, each having a duration on the order of a few milliseconds to tens of milliseconds;

based on the first total radiation dose, determining a dose error associated with the first location for the first treatment fraction;

based on the dose error, determining a second total radiation dose to be delivered to the first location in a second treatment fraction;

based on the second total radiation dose, changing a time-resolved machine state of the radiotherapy system associated with the second treatment fraction to a modified time-resolved machine state; and delivering the second total radiation dose to the first location using the modified time-resolved machine state.

15. The computer-implemented method of claim 14, wherein the first time-resolved machine state includes a set of values for one or more process parameters associated with the radiotherapy system, wherein each of the one or more process parameters effects at least one of a location of radiation delivery within the region during the first treatment fraction and intensity of radiation delivery within the region during the first treatment fraction.

16. The computer-implemented method of claim 15, wherein the set of values for one of the one or more process parameters comprises a value for each time segment of the first treatment fraction.

17. The computer-implemented method of claim 14, wherein the modified time-resolved machine state includes a set of values for one or more process parameters associated with the radiotherapy system, wherein each of the one or more process parameters effects at least one of a location of radiation delivery within the region during the second treatment fraction and intensity of radiation delivery within the region during the second treatment fraction.

18. The computer-implemented method of claim 17, wherein changing the time-resolved machine state of the radiotherapy system associated with the second treatment fraction comprises changing at least one value in the set of values.

19. The computer-implemented method of claim 14, wherein determining the first total radiation dose comprises:

based on the time-resolved surface map of the region, generating a different modified digital volume of the region for each time segment in the plurality of time segments included in the first treatment fraction; and for each time segment in the plurality of time segments, determining an incremental radiation dose that is delivered during the time segment to the first location.

20. The computer-implemented method of claim 19, wherein the first total radiation dose comprises a sum of the incremental radiation doses for each time segment in the plurality of time segments.

\* \* \* \* \*